United States Patent [19]

Theeuwes et al.

[11] Patent Number: 5,232,438
[45] Date of Patent: * Aug. 3, 1993

[54] MEMBRANE FOR ELECTROTRANSPORT TRANSDERMAL DRUG DELIVERY

[75] Inventors: Felix Theeuwes; J. Richard Gyory, both of Los Altos; Ronald P. Haak, Cupertino, all of Calif.

[73] Assignee: Alza Corporation, Palo Alto, Calif.

[*] Notice: The portion of the term of this patent subsequent to May 22, 2007 has been disclaimed.

[21] Appl. No.: 898,618

[22] Filed: Jun. 15, 1992

Related U.S. Application Data

[63] Continuation of Ser. No. 648,269, Jan. 30, 1991, Pat. No. 5,169,382, which is a continuation of Ser. No. 252,402, Oct. 3, 1988, Pat. No. 5,080,646.

[51] Int. Cl.$^5$ ............................................. A61N 1/30
[52] U.S. Cl. ........................................ 604/20; 604/49; 128/802
[58] Field of Search ............... 604/20, 49; 128/798, 128/802, 803

[56] References Cited

U.S. PATENT DOCUMENTS

| | | | |
|---|---|---|---|
| 3,797,494 | 3/1974 | Zaffaroni | 128/268 |
| 4,144,317 | 3/1979 | Higuchi | 424/21 |
| 4,274,420 | 6/1981 | Hymes | 128/641 |
| 4,325,367 | 4/1982 | Tapper | 128/207.21 |
| 4,391,278 | 7/1983 | Cahalan et al. | 128/640 |
| 4,419,092 | 12/1983 | Jacobsen et al. | 604/20 |
| 4,457,748 | 7/1984 | Lattin et al. | 604/20 |
| 4,474,570 | 10/1984 | Ariura et al. | 604/20 |
| 4,557,723 | 12/1985 | Sibalis | 604/20 |
| 4,573,996 | 3/1986 | Kwiatek et al. | 604/897 |
| 4,588,580 | 1/1989 | Gale et al. | 424/21 |
| 4,622,031 | 11/1986 | Sibalis | 604/20 |
| 4,640,689 | 2/1987 | Sibalis | 604/20 |
| 4,673,565 | 6/1987 | DiLuccio et al. | 424/443 |
| 4,689,039 | 8/1987 | Masaki | 604/20 |
| 4,702,732 | 10/1987 | Powers et al. | 604/20 |
| 4,708,716 | 11/1987 | Sibalis | 604/20 |
| 4,713,050 | 12/1987 | Sibalis | 604/20 |
| 4,722,726 | 2/1988 | Sanderson et al. | 604/20 |
| 4,731,049 | 3/1988 | Parsi | 604/20 |
| 4,731,926 | 3/1988 | Sibalis | 29/877 |
| 4,842,577 | 6/1989 | Konno et al. | 604/20 |
| 4,904,247 | 7/1990 | Therriault et al. | 604/304 |
| 4,927,408 | 5/1990 | Haak et al. | 604/20 |
| 4,940,456 | 7/1990 | Sibalis et al. | 128/798 |
| 5,080,646 | 1/1992 | Theeuwes et al. | 604/20 |
| 5,147,296 | 9/1992 | Theeuwes et al. | 604/20 |

FOREIGN PATENT DOCUMENTS

| | | |
|---|---|---|
| 0208395 | 1/1987 | European Pat. Off. |
| 0249343 | 12/1987 | European Pat. Off. |
| 0278474 | 8/1988 | European Pat. Off. |
| 2174605 | 11/1986 | United Kingdom |

OTHER PUBLICATIONS

P. Tyle & B. Kari, "Iontophoretic Devices," in Drug Delivery Devices, pp. 421–454 (1988).

Ashburn, Michael A.; Stephen, Robert L.; Ackerman, Eric; Petelenze, Tomas J.; Hare, Bradford; Pace, Nathan L.; and Hofman, Aaron A., "Iontophoretic Delivery of Morphine for Postoperative Analgesia", Journal of Pain and Sympton Management, vol. 7, No. 1, Jan., 1992, pp. 27-33.

Preat V., vanDamme F., Tshilanda E. and Thysman S., "Iontophoretic Transport of Fentanyl and Sufentanyl" from Proceed. Intern. Symp. Control. Rel. Bioact. Mater., 18 (1991), Controlled Release Society, Inc. pp. 605 to 606.

Primary Examiner—C. Fred Rosenbaum
Assistant Examiner—Michael Rafa
Attorney, Agent, or Firm—D. Byron Miller; Steven F. Stone; Edward L. Mandell

[57] ABSTRACT

A membrane capable of inhibiting agent release from a delivery system when no electrical current is flowing and yet provide minimal impedance to electrically-assisted agent delivery, useful both for incorporating into electrotransport agent delivery systems and for use in measuring agent release rates in in vitro testing.

24 Claims, 2 Drawing Sheets

MEMBRANE FOR ELECTROTRANSPORT TRANSDERMAL DRUG DELIVERY

This is a continuation of application Ser. No. 07/648,269 filed Jan. 30, 1991, now U.S. Pat. No. 5,169,382, which in turn is a continuation of application Ser. No. 07/252,402 filed Oct. 3, 1988, now U.S. Pat. No. 5,080,646.

FIELD OF THE INVENTION

This invention relates to electrotransport agent delivery. More particularly, this invention relates to a membrane capable of controlling the release of agent from an electrotransport agent delivery system where passive delivery is inhibited but not delivery under an electric current. Still more particularly, but without limitation thereto, this invention relates to a membrane suitable for use in the in vitro testing of release rates of electrotransport agent delivery devices.

BACKGROUND OF THE INVENTION

Many drugs are not suitable for passive drug delivery because of their size, ionic charge characteristics and hydrophilicity. One method of overcoming this limitation in order to achieve transdermal administration of such drugs is the use of electrical current to actively transport drugs into the body, as for example, through intact skin. This concept is based upon basic principles of electrochemistry. An electrochemical cell in its simplest form consists of two electrodes and associated half cell reactions, between which electrical current can flow. Electrical current flowing through the metal portion of the circuit is carried by electrons (electronic conduction), while current flowing through the liquid phase is carried by ions (ionic conduction). Current flows as electrical charge is transferred to chemical species in solution by means of oxidation and reduction charge transfer reactions at the electrode surfaces. A detailed description of the electrochemical processes involved in electrically-assisted drug transport can be found in electrochemistry texts such as J. S. Newman, Electrochemical Systems (Prentice Hall, 1973) and A. J. Bard & L. R. Faulkner, Electrochemical Methods, Fundamentals and Applications (John Wiley & Sons, 1980). Therefore, only pertinent portions will be presented here.

Electrically-assisted transport or electrotransport, is defined as the mass transport of a particular chemical species in the presence of an electric potential. Typically, said transport is through a biological interface or membrane when the electrical potential gradient is imposed across it. Three physical processes contribute to transport under these conditions: passive diffusion, electromigration and convection.

The Nernst-Planck equation (1) expresses the sum of these fluxes for any particular chemical species i in the presence of an electrical field, $\Delta\Phi$.

$$J_i = -[D_i \Delta C_i] - [z_i F u_i C_i \Delta \Phi] + [C_i v] \quad (1)$$

where
$J_i$ = flux of species i (moles/cm$^2$−sec)
$D_i$ = diffusion coefficient of i (cm$^2$/sec)
$\Delta$ = the gradient operator
$C_i$ = concentration of i
$z_i$ = number of charges per molecule of i
F = Faraday's constant (96,500 coulombs/mole of charge)
$u_i$ = mobility of i (velocity/force = sec/g)
$\Phi$ = electrical potential (volts)
v = velocity vector (cm/sec)

The Nernst-Plank equation (1) has three terms, one for each of the physical processes contributing to the mass transport. The first term is the flux due to passive diffusion and is proportional to the concentration gradient of species i. The second term is the flux due to electromigration, where the driving force is the gradient of electrical potential, i.e., the electric field strength. The third term is the flux due to convection or electroosmosis, where the mechanism of transport is the movement of material by bulk fluid flow which is determined by the magnitude and direction of the bulk fluid velocity vector.

Considering transport in only one direction of a rectilinear coordinate system, equation (1) may be simplified to:

$$J_{i,x} = -[(D_i)(dC_i/dX)] + ]z_i F u_i C_i E_x] + [C_i v_x] \quad (2)$$

where
$J_{i,x}$ = the total electrically-assisted flux of species i in the x direction
$E_x = -(d\Phi/dx)$ = the electrical field in the x direction i.e. the negative of the electrical potential gradient
$v_x$ = the x component of the velocity vector Equation (2) applies within each and every phase, and the physical constants and extensive properties must be applicable to the phase of interest. For the case of an electrotransport transdermal system positioned on the skin, one form of equation (2) holds within the drug containing reservoir of the electrotransport system where $D_i$, $c_i$, $u_i$, etc., are the diffusion coefficient, concentration and mobility of species i within the system. Another identical form of equation (2) holds within the skin (assuming the skin is uniform) except that the diffusion coefficient, concentration and mobility of species i are now those within the skin. The extensive properties of these equations such as the concentration and electric field strength are linked at the interface by an appropriate proportionality constant such as the partition coefficient and the ratio of dielectric constants, respectively.

The second term in equation (2) describes the flux due to electromigration. Typically written in terms of the electrical field, it is often more convenient to express electromigration in terms of the electrical current. By using the transference number of species i, $t_i$, which is the fraction of current carried by species i, the electromigration flux of species i, $J_{i,EM}$, may be expressed as the product of the transference number and the current density passing through the medium:

$$J_{i,EM} = [(t_i)(I)]/A \quad (3)$$

where
I = the total current passing through the medium
A = the area through which the current passes The third term in equation (2) describes the flux due to convection. Disregarding the possibility of significant hydrostatic pressure gradients across the membrane or chemical osmosis driving forces, and assuming the membrane has a fixed surface charge, it can be said that the only means of moving an appreciable amount of fluid across a membrane is through electroosmosis. Electroosmosis is defined as bulk fluid flow entrained by the migration of unpaired excess ions moving in response to an applied electric field. The electroosmotic flux of species i, $J_{i,EO}$, is related to the total current passing through the membrane by the following equation:

$$J_{i,EO} = (\epsilon \zeta I)/(\kappa^* \mu A) \tag{4}$$

where
- $\epsilon$ = the dielectric constant of the liquid medium
- $\zeta$ = the zeta potential of the membrane having a fixed charge
- $\kappa$ = the conductivity of the liquid phase
- $\mu$ = the viscosity of the liquid phase Equations (3) and (4) demonstrate that the second and third terms of equation (2) may be written as functions of the total current passed through a system. Hereinafter, the sum of these two terms will be referred to as the electrokinetic flux, $J_{EK}$.

As stated earlier, the first term of equation (2) is the passive diffusion term. This term is identical to that when passive diffusion is the only mechanism of mass transfer, i.e., it is independent of the electrical conditions of the system. This term will hereinafter by referred to as the passive flux component, $J_P$. The sum of all three terms in equation (2) will be called the electrically-assisted flux, $J_{EA}$:

$$J_{EA} = J_P + J_{EM} + J_{EO} \tag{5}$$

Since the electrokinetic flux, $J_{EK}$, is the sum of the flux due to electromigration and the flux due to electroosmosis, equation (5) can be simplified to:

$$J_{EA} = J_P + J_{EK} \tag{6}$$

A membrane which mimics the behavior of skin must exhibit the following mass transport properties: transport by convection should be negligible at high ionic strength, resistance to passive diffusion should be high, and resistance to electromigration should be relatively low. Ideally, when no electric field is imposed on the membrane, i.e., no current is passed across the membrane, no drug flux should be detected. When a field is applied and current is caused to flow across the membrane, appreciable drug flux should be detected. Furthermore, a relatively small voltage should be required in that a 100 $\mu A/cm^2$ current would require less than 1 volt.

The concept of electrotransport in drug delivery is known, and there are a number of categories in which drug delivery systems utilizing electrotransport principles can offer major therapeutic advantages. See P. Tyle & B. Kari, "Iontophoretic Devices" in DRUG DELIVERY DEVICES, pp. 421-454 (1988). There is a continuing need to develop systems with improved characteristics, specifically improved control of the drug delivery. State of the art rate controlling membranes such as are taught in U.S. Pat. No. 3,797,494, are suitable for passive transport but do not provide control over electrically-assisted delivery. Therefore, there is a need for a membrane which may be used to limit or control the electrically-assisted release from the system. Further, there is a need for an electrotransport drug delivery system which has a control membrane to inhibit the release of drug from the system when no current is flowing. The main feature is that use of such a membrane, by eliminating or greatly reducing passive transport, would allow release of the drug to be turned on and off, by simply turning the electric field (current) on and off.

Such a membrane would also provide a safety feature to prevent excess drug delivery from occurring if the electrotransport system is placed on abraded skin or on a body surface which has somehow been compromised. Further, such a safety feature would inhibit drug release during handling of the system.

Along with the growing interest in the development of electrotransport systems, there is a growing need for improved techniques of testing the properties of said systems. For example, state of the art techniques for measuring the in vitro release rates of passive transdermal systems are inadequate for testing electrotransport systems. Typically, such testing utilizes a synthetic membrane such as Hytrel ® or an ethylene vinyl acetate copolymer such as EVA 9, which exhibit characteristics similar to that of skin during passive drug diffusion. There is a need for a synthetic membrane that exhibits electrically-assisted ionic transport properties similar to that of skin.

Another use for such a membrane would be for system stability testing. Human cadaver skin cannot be used for this application because of the extent of natural donor to donor variation and large supplies are often needed for quality control, which are not always readily available. For stability testing, a membrane must behave consistently over time in order to provide an accurate measure of system stability.

SUMMARY OF THE INVENTION

An object of this invention is to provide an improved approach and means for providing system control within an electrotransport agent delivery system.

Another object of this invention is to provide for electrically-assisted delivery of agents with a safety mechanism to insure that agent is only released during those periods when the current is on.

A still further object of this invention is to develop a membrane which will allow passage of agent when under the influence of an electric current and which will also be a barrier to the passage of the same agent when not under the influence of an electric current, for use as release rate controlling membranes or as separator membranes.

Another object of this invention is to develop a membrane model for skin having consistent and reliable transport properties, to provide the capability for performing accurate measurements of the in vitro release rate of drug from electrotransport delivery systems, and to perform system stability studies.

These and other objects, features and advantages of the invention have been demonstrated by the present invention wherein an electrotransport agent delivery system for placement on a body surface is comprised of: a backing member; a source of electrical power; a first and a second current conducting member; a reservoir means containing an agent to be delivered; means for maintaining said system in current conducting and agent transmitting relationship to said body surface; and a means for controlling agent delivery positioned between said reservoir means and said body surface.

BRIEF DESCRIPTION OF THE DRAWING

The invention will be described in further detail with reference to the accompanying drawings wherein.

DESCRIPTION OF THE INVENTION

The composite membrane of this invention exhibits larger electrically-assisted transport than passive. When no current flows through the system, passive drug diffusion from the system is negligible or insignificant. The method of evaluating suitable composite membranes consists of determining the electrokinetic and the passive flux of a compound through the membranes and using their ratio as a measure of the ability of these membranes to behave as required.

Passive transport of ionic compounds may be eliminated entirely by a hydrophobic membrane. However, the electrical resistance of such a membrane is prohibitively high. In order to reduce electrical resistance, some hydrophilic pathways must be provided but not so many that passive diffusion is large. This may be done by use of a microporous membrane having a few continuous aqueous paths, or by use of an ion exchange membrane. This invention is a composite membrane having properties of both types of membranes wherein a hydrophilic resin, such as an ion exchange resin, is blended into a hydrophobic polymeric matrix. The resin has a high permeability for agent and provides a complex of "microporous" ion exchange pathways. The hydrophobic polymer has a low permeability for agent and provides a non-permeable hydrophobic matrix structure. The membrane can be manufactured by solvent casting, melt processing or extrusion.

A microporous membrane limits diffusion simply by limiting the number of pathways available. Ion exchange membranes limit diffusion by a more complex mechanism. Ion exchange membranes have either a fixed negative or a fixed positive charge. The fixed charge is compensated by unbound or covalently bound compounds having the opposite charge, i.e., counter- or co-ions. The fixed charge is bound to the membrane and is not free to move, thereby causing the entire membrane to be charged and inhibiting ions of like charge from passing through the membrane. Maintenance of electroneutrality prevents the co-ion from passively diffusing. Therefore, passive diffusion of ionic compounds is prevented because one of the ions can not penetrate the membrane.

Rejection of a particular ion occurs when the fixed charge on the membrane has the same sign as the ion. When current is passed, the ions having a charge opposite to that of the fixed charge of the membrane, will have a higher transference number through the membrane than will the ions having the same charge as the membrane. Therefore, an anion exchange membrane having a positive fixed charge may exhibit very low passive transport of a positively charged species, but the electrically-assisted transport of that species may also be low. Conversely, a cation exchange membrane having a negative fixed charge may have a higher passive transport of positively charged species, but it will also exhibit larger electrically-assisted transport of these species. It is not obvious which of these membrane types will exhibit the best $J_{EK}/J_P$ ratio (the ratio of the electrokinetic to the passive flux) in this situation.

We have found that by blending a small amount of resin within a hydrophobic matrix, the total water content and density of hydrophilic pathways through an otherwise hydrophobic membrane, may be controlled. Also, the charge density within these pathways remains relatively high, which would not occur if the hydraulic permeability of a normal ion exchange membrane was controlled by merely changing the fixed charge density within the membrane.

Upon further analysis of the composite membranes of this invention, we have found that the process of blending a small amount of hydrophilic resin within a hydrophobic matrix actually enhances the $J_{EK}/J_P$ ratio of the membrane. The passive flux of the species of interest for a unit area of pure ion exchange resin and pure hydrophobic matrix material is given by the expressions $J_{RP}$ and $J_{MP}$, respectively. For a membrane having a uniform dispersion of resin within matrix material, the fraction of surface area which is resin material is identical to the volume fraction of resin within the membrane. Therefore, the passive flux per unit area of composite membrane, $J_P$, is given by:

$$J_P = [(\Theta)(J_{RP})] + [(1-\Theta)(J_{MP})] \qquad (7)$$

where $\Theta$ is the volume fraction (area fraction) of ion exchange resin based on the total volume of the composite membrane.

It may be assumed that when current is passed, only the volume occupied by the ion exchange resin will contribute to the electrokinetic flux, $J_{EK}$, i.e., there is no ionic conduction or electroosmotic flow through the hydrophobic matrix material. Therefore, the electrokinetic flux may be written as:

$$J_{EK} = [((t_D)(I))/A] + [(\epsilon \zeta I)/(\kappa^* \mu A)] \qquad (8)$$

where $t_D$ is the transference number of the drug through the ion exchange resin. Equation (8) shows that the electrokinetic flux based upon unit area of composite membrane is independent of the volume fraction of resin. Even though the flux may be independent of loading, the voltage required to achieve the specific current, I, is not. As resin loading is decreased, the voltage required to pass the specific current will increase. This follows from Ohm's Law V=IR, where as loading increases the resistance (R) increases since R is an area independent term, thus increasing the voltage (V).

The ratio of the electrokinetic to the passive flux is determined by:

$$J_{EK}/J_P = \frac{[((t_D)(I))/A] + [(\epsilon \zeta I)/(\kappa^* \mu A)]}{[(\Theta)(J_{RP})] + [(1-\Theta)(J_{MP})]} \qquad (9)$$

If the solution next to this composite membrane has a relatively high ionic strength then the electroosmotic component of equation (9) will be small. Also, if the passive diffusion of the drug is small through the hydrophobic matrix compared to that through the ion exchange portion of the composite membrane, the term in the denominator involving $J_{MP}$ may also be eliminated. Therefore, the electroosmotic and matrix passive diffusion terms may be eliminated from equation (9). Yet another substitution may be made, specifically, the passive flux through the resin may be written in terms of the diffusion coefficient and concentration gradient. Assuming that the drug concentration on the receptor side of the membrane is essentially zero and that the concentration gradient within the membrane is linear, $J_{RP}$, may be written as:

$$J_{RP} = [(D)(C_D)]/l \tag{10}$$

where
  $D$ = the diffusion coefficient of the drug through the resin
  $C_D$ = the drug concentration in the resin on the donor side of the membrane
  $l$ = the thickness of the membrane
Therefore, equation (9) can be simplified to:

$$J_{EK}/J_P = (t_D I l)/(\Theta D C_D A) \tag{11}$$

This simplified form indicates that $J_{EK}/J_P$ is inversely proportional to the volume fraction of resin, and therefore, the $J_{EK}/J_P$ ratio should increase as the resin loading is decreased. From equation (11), it also can be predicted that thicker membranes should exhibit a larger $J_{EK}/J_P$ ratio since the passive flux would decrease for thicker membranes without affecting the electrokinetic flux. However, a higher voltage would be required. The only direct influence electromigration has on the $J_{EK}/J_P$ ratio is through the transference number of the drug. This number is preferably maximized and therefore, an ion exchange resin having a fixed charge of opposite charge than that of the drug species of interest, is desirable.

Equation (11) also indicates that it may be advantageous to operate at a low donor drug concentration. However, the transference number, $t_D$, also depends on the drug concentration, but it is not a linear dependence. For large transference numbers, $t_D$ is nearly independent of concentration. However, for small transference numbers, $t_D$ is linearly dependent on donor concentration. Therefore, reducing the donor drug concentration will only increase the $J_{EK}/J_P$ ratio if the transference number of the drug through the resin is high. Equation (11) also suggests a convenient means of characterizing membranes comprised of various materials since the $J_{EK}/J_P$ ratio is predicted to be inversely proportional to the resin loading.

The only other piece of information required to determine the utility of a particular combination of materials is the resistance the membrane provides against electrokinetic transport. This may be measured by placing a reference electrode on either side of a membrane while current is being passed and recording the potential difference with an electrometer. The resistance of a membrane used for system testing is not a critical factor because power consumption is of little consequence for testing purposes. However, for use in an actual system, low resistance is critical. It is desirable to limit the voltage requirements imposed by a control membrane to be less than 1 volt at a current density of 100 $\mu A/cm^2$, i.e., the membrane resistivity should be less than 10 $k\Omega - cm^2$.

Control membranes can be fabricated using a variety of suitable hydrophobic polymeric materials, including without limitation, polycarbonates, i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, cellulose, collodion, epoxy resins, olefins such as polyethylene and polypropylene, porous rubber, cross-linked poly(ethylene oxide), cross-linked polyvinylpyrrolidone, cross-linked poly(vinyl alcohol); derivatives of polystyrene such as poly (sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers, particularly those having 1–40 weight percent vinyl acetate content, such as those described in U.S. Pat. No. 4,144,317, incorporated herein by reference, polyamides, polyurethanes, polyethylene oxides, polyox, polyox blended with polyacrylic acid or Carbopol®, cellulose derivatives such as hydroxypropyl methyl cellulose, hydroxyethyl cellulose, hydroxypropyl cellulose, pectin, starch, guar gum, locust bean gum, and the like, along with blends thereof. This list is merely exemplary of the materials suited for use in this invention. A more extensive list can be found in J. R. Scott & W. J. Roff, Handbook of Common Polymers (CRC Press, 1971) and in patents disclosing suitable materials for use in manufacturing microporous membranes such as U.S. Pat. No. 3,797,494, incorporated herein by reference.

Suitable hydrophilic resins include materials such as cross-linked polyvinylpyrolodone. Particularly suitable hydrophilic materials are ion exchange resins having ion exchange functional groups such as sulfonic acid, carboxylic acid, iminodiacetic acid and quaternary amines. These include, without limitation, the commercially available cation and anion resins listed below. Selection of an ion exchange resin is determined by the charge of the drug being delivered.

| NAME (BACKBONE) | FORM | SIZE mesh | DRY meq/g | RESIN BED meq/mL | MOISTURE % of total | PORE SIZE |
| --- | --- | --- | --- | --- | --- | --- |
| Cation Exchange Resins | | | | | | |
| AG 50W-X12* | H | 100–200 | 5 | 2.3 | 42–48 | small |

-continued

| NAME (BACKBONE) | FORM | SIZE mesh | DRY meq/g | RESIN BED meq/mL | MOISTURE % of total | PORE SIZE |
|---|---|---|---|---|---|---|
| (Sulfonic acid) | | | | | | |
| Bio-Rex ® 70* (Carboxylic acid) | Na | 200–400 | 10.2 | 3.3 | 65–74 | large |
| Chelex ® 100* Chelating resin (Iminodiacetic acid) | Na | 100–200 | 2.9 | 0.7 | 71–76 | large |
| Amberlite IR-120** (Sulfonic acid) | H | 20–50 | 5.0 | 1.8 | 49–55 | medium |
| Anion Exchange Resins | | | | | | |
| AG 1-X8* ($R_4N^+$) | Cl | 20–50 | 3.2 | 1.4 | 39–45 | medium |
| Amberlite IRA-400** ($RN(CH_3)_3^+$) | Cl | 20–50 | 3.3 | 1.2 | 42–48 | medium |

*represents Trademark names of Bio-Rad
**represents Trademark names of Mallinckrodt The incorporation of composite membranes according to this invention into electrotransport agent delivery systems, along with providing system control, also provide an important safety feature. The passive release of drug from a system which does not have such a control membrane can be very high. This is normally not a problem, since the hydrophilic compounds delivered using such systems do not easily penetrate the skin via passive diffusion, i.e., the skin itself is a blocking membrane. However, if the skin is compromised in some manner, such as being cut or scraped, a harmful dose of drug could be delivered. When a composite membrane according to this invention is incorporated into an electrotransport system, the passive release of drug from the system is inhibited. In a system having such a membrane, the release of drug from the system would be predominantly controlled by the magnitude of the electrical current. Therefore, even if the skin is compromised, the amount of drug released from the system will be controlled to some tolerable level.

It is believed that this invention has utility in connection with the delivery of drugs within the broad class normally delivered through body surfaces and membranes, including skin, mucosa and nails. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

We have demonstrated the utility of this invention in connection with the delivery of metoclopramide. It is anticipated that this invention will prove to be useful in the controlled delivery of baclofen, betamethasone, beclomethasone, doxazosin, droperidol, fentanyl, sufentanil, leuprolide, lidocaine, methotrexate, micanazole, prazosin, piroxicam, verapamil, tetracaine, diltiazam, indomethacin, hydrocortisone, terbutaline and encainide. It is preferable to use the most water soluble form of the drug or agent to be delivered, which in most instances is the salt form.

The membrane of this invention is suited to control both the release of agent from electrodes or electrotransport systems. This application for our invention is best understood with reference to the accompanying drawings. In general terms, this invention can be used in conjunction with any state of the art electrotransport delivery systems such as those described in U.S. Pat. Nos. 4,325,367; 4,474,570; 4,557,723; 4,640,689; and 4,708,716; all of which are incorporated herein by reference. Similarly, this invention can be utilized with any state of the art electrodes which are attached to an external power source, such as those described in U.S. Pat. Nos. 4,274,420; 4,391,278; 4,419,092; and 4,702,732; all of which are incorporated herein by reference. The composite membrane of this invention can be manufactured as an integral part of a system or it can be manufactured separately with adhesive layers or some suitable means for adhering so that it may subsequently be affixed to any state bf the art electrode or electrotransport system.

Figure 1:
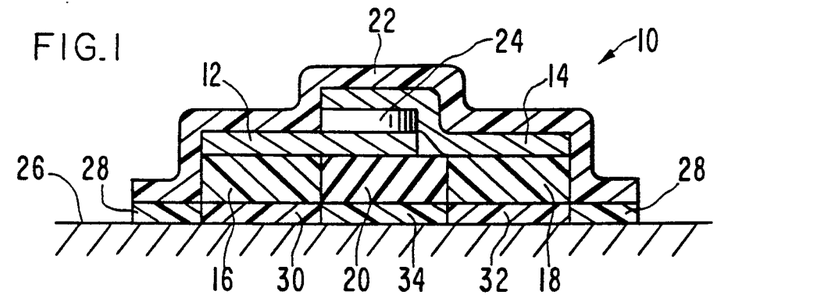
FIG. 1 is a schematic cross sectional view of the membrane of this invention incorporated into an electrotransport transdermal therapeutic system having a peripheral adhesive layer, where electrical power is supplied by an integral power source.

FIG. 1 is a typical example of an electrotransport system utilizing the composite membrane of this invention. System 10 has two current conducting members, referred to herein as a donor electrode 12 and a counter electrode 14. The electrodes can be metal foils, metal powder in a polymeric matrix, or any other electrically conductive material. The donor and counter electrodes are positioned adjacent to the donor electrode pad 16 which contains the agent to be delivered, and counter electrode pad 18, respectively. The pads can be polymeric matrices or gel matrices, for example, and are separated by an insulator 20 made of a non-conducting polymeric material. The system has a backing layer 22 made of an electrically insulating or non-conductive material such as is commonly used in transdermal systems. Electrical power is supplied by power source 24 which can be a battery or a series of batteries positioned between the electrodes 12 and 14 such that the electrode 12 is in direct contact with one pole of the power supply and electrode 14 is in direct contact with the opposite pole. The system adheres to the body surface 26 by means of a peripheral adhesive layer 28. The system would normally include a strippable release liner, not shown.

Composite membrane 30 is positioned between the donor electrode pad 12 and the body surface 26, so as to control drug release from the pad. In one type of electrotransport system, the donor electrode pad 14 contains the drug (salt form) to be delivered and the counter electrode pad 16 contains a suitable electrolyte. Another type of electrotransport system places drug in both electrode pads and in that manner both pads would function as donor electrode pads. For example, positive ions could be introduced into tissues from the anode (positive electrode), while negative ions could be introduced from the cathode (negative pole). In that instance, layer 32 positioned between the counter electrode pad 18 and the body surface 26 would also be a composite membrane.

Layer 34 is a barrier to avoid transference of ions across the body surface, and can be an air gap, a non-ion conducting adhesive or other suitable barrier to ion flow. The composite membrane of this invention can also be used in a system embodiment where layers 32 and 34 are omitted and instead, the counter electrode pad 18 and insulator 20 are designed so as to be in direct contact with the body surface 26.

Figure 2:
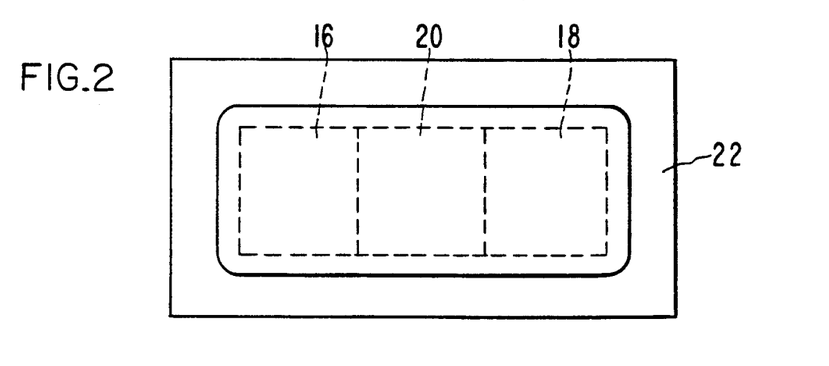
FIG. 2 is a top view of the embodiment of FIG. 1.

FIG. 2 illustrates a top view of the system of FIG. 1 to show the parallel alignment of the components. In this configuration, the composite membrane 30 is rectangular in shape. However, this invention contemplates use in systems which have their components aligned peripherally, in a circular configuration for example, and the composite membrane would be designed accordingly.

The size of the composite membrane of this invention can also vary with the size of the system or electrode involved and can be within the range of from less than 1 cm$^2$ to greater than 200 cm$^2$. The average system however, has a size within the range of about 5-50 cm$^2$. Similarly, the composite membrane will likely be within that range.

Figure 3:
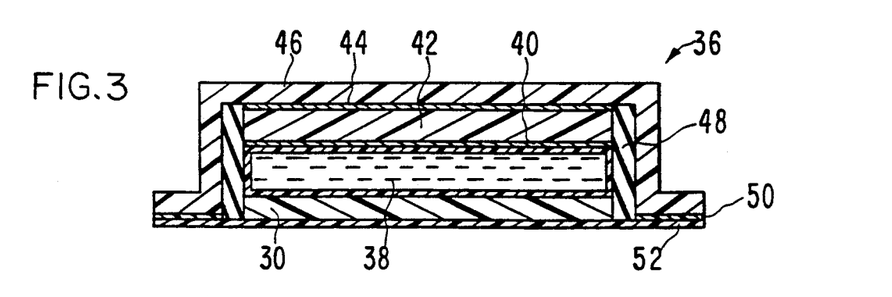
FIG. 3 is a schematic cross sectional view of the membrane of this invention incorporated into another electrotransport transdermal therapeutic system.

FIG. 3 illustrates another type of electrotransport system 36 suitable for use with the composite membrane 30 of this invention. System 36 has an agent reservoir 38 which can be in the form of a flexible bag as shown or a matrix as in system 10; a first current conducting membrane 40 positioned between reservoir 38 and battery 42; and a second current conducting member 44 positioned between reservoir 38 and a conductive backing member 46. The system has an insulating member 48 and a peripheral ion-conducting adhesive 50. The system is packaged with a strippable release liner 52. Suitable system materials are disclosed in U.S. Pat. No. 4,713,050, incorporated herein by reference.

Figure 4:
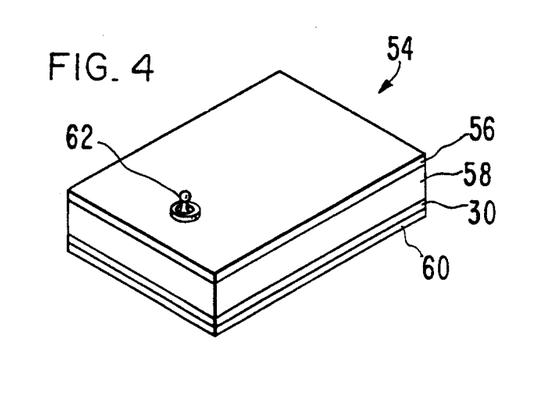
FIG. 4 is a perspective view of an embodiment of the invention incorporated into a single electrode unit.

FIG. 4 illustrates an electrode 54 suitable for use with the composite membrane 30 of this invention. Electrode 54 has a current conducting member 56, an agent reservoir 58 and composite membrane 30. The electrode adheres to the body surface by means of an ion-conducting adhesive layer 60. The electrode 54 has a fastener 62 by which it can be connected to an external current supply. Suitable electrode materials are disclosed in U.S. Pat. No. 4,274,420, incorporated herein by reference.

Figure 5:
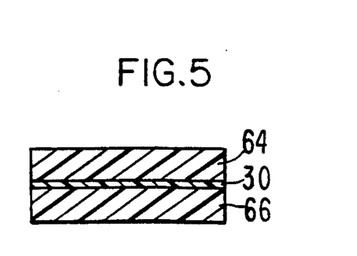
FIG. 5 is a schematic cross sectional view of the membrane of this invention when used as a separator.

The membrane of this invention may also be used to keep the electrolyte and agent somewhat separated during storage. This is shown in FIG. 5. Since the composite membrane 30 inhibits release from a delivery system when no electrical current is flowing, it will also function to inhibit release from a reservoir within a delivery system. In FIG. 5, reservoir 64 contains electrolyte and reservoir 66 contains the agent to be delivered. Membrane 30 serves to minimize the passage of components from reservoir 64 into reservoir 66 and vice versa. Once the electrical current begins to flow, the components of reservoir 64 are free to move across membrane 30.

Composite membranes according to this invention can also be used for the in vitro evaluation of agent or drug release rates of electrotransport systems. In order to perform such an evaluation using a synthetic membrane, the membrane must have electrically-assisted transport characteristics similar to that of human skin where the passive transdermal permeation rate for hydrophilic compounds is often very low compared to the electrically-assisted permeation rate. The membrane of this invention meets such requirements.

An evaluation of the agent release characteristics of an electrotransport system using a composite membrane according to this invention involves the placement of the complete system on the surface of the composite membrane, adequately supported underneath, having a reservoir of receptor solution positioned on the opposite side of the membrane. If no such controlling membrane was used, i.e., if a microporous membrane was employed, then agent would quickly be released from the system via passive diffusion. When a composite membrane according to this invention is used for the test, the passive transport of agent into the receptor solution is inhibited. When the electrotransport system is placed in contact with the composite membrane, electrical current can flow, thus providing electrically-assisted transport of agent into the receptor solution.

The testing can provide several important system characteristics including, the amount of agent contained in the system, the magnitude of electrical current flowing through the system, the agent discharge profile as a function of time, and the discharge capacity of the electrical power source.

Having thus generally described our invention, the following examples will illustrate how variations of the above described parameters provide therapeutically effective electrotransport systems.

EXAMPLE I

Commercially available polypropylene and polyethylene based microporous membranes (Cellgard ® manufactured by Celanese), polycarbonate and polyester microporous membranes (Nuclepore ®), cellulose and cellulose acetate membranes with varying amounts of triacetin and a porous glass material (Vycor ®, Corning No. 7930) were cut to the appropriate size and used as supplied. Pore sizes ranged from 40 Å for the porous Vycor ® to 0.2 μm for Cellgard ® and were undetermined for the cellulose based materials.

The transport properties of these membranes were evaluated by measuring the passive and electrically-assisted flux of metoclopramide (MCP) across each membrane. This was done using a two compartment cell. Drug solution was placed in the anode (donor)

compartment and the cathode (receptor) compartment solution was periodically sampled and evaluated for MCP content. The donor solution was 0.1 g MCP/g water. The receptor solution was Dulbecco's phosphate buffered saline (DPBS), a mixture of salts made to mimic interstitial fluids with a total salt concentration of 0.15M and the pH adjusted to 7. DPBS is commercially available from Gibco. The experimental temperature for all experiments was 32° C. Cells operating under passive conditions had zero current applied while cells operating under active or electrically-assisted conditions had 100 $\mu A/cm^2$ applied such that positive ions migrated from the donor to the receptor compartment and negative ions migrated from the receptor to the donor compartment. In this manner, the electrode next to the donor solution was the anode and that next to the receptor solution was the cathode. At sampling time, all of the receptor solution was removed and replaced with fresh DPBS. The samples were analyzed for MCP content using UV-absorbance at 310 nm.

None of the commercially available microporous membranes evaluated provided satisfactory results. Either current could not be passed through the membrane, as for some of the Cellgard ® and cellulose acetate membranes, or the passive transport of MCP greatly outweighed the electrokinetic transport, thereby making the measured flux with and without applied current indistinguishable.

EXAMPLE II

Commercially available ion exchange membranes evaluated were of the strong acid or strong base type. They were cut to size and then soaked in a saturated sodium chloride solution. This pretreatment ensured that the co-ion of the membranes fixed charge would be either sodium or chloride. The transport properties of these materials were evaluated as in Example I. The anion exchange membranes tested were Raipore 1030, Raipore 4030 and Raipore 5030. These showed no appreciable difference in MCP flux for either passive or electrically-assisted transport. The cation exchange membranes tested were Nafion ®, Raipore 1010, Raipore 4010 and Raipore 5010. Nafion ® and Raipore 5010 exhibited very small steady state MCP fluxes. The flux of MCP through Raipore 1010 indicated that the passive component exceeded the electrokinetic component to a large degree and therefore, both electrically-assisted and passive fluxes were comparable. The only membrane to show any significant difference between electrically-assisted and passive transport, was Raipore 4010. The Raipore 4010 exhibited a lag time on the order of 3 hours, which is desirable for certain drug delivery patterns.

EXAMPLE III

Composite membranes according to this invention were made using the following materials. Three resins were used: cross-linked polyvinylpyrolodone (PVP-xl), a wettable resin which picks up a slight positive charge due to hydrogen ion adsorption at amine sights, Bio-Rex ® 70, a macroreticular acrylic polymer based carboxylic acid cation exchange resin made by Bio-Rad Laboratories, and Chelex ® 100, a styrene divinylbenzene lattice with paired iminodiacetate cation exchange groups also made by Bio-Rad Laboratories. Two particle sizes of Chelex ® 100 were used, <400 mesh and 100–200 mesh. All films containing PVP-xl were made with ethylene vinyl acetate having a 28 weight percent vinyl acetate content (EVA 28) as a matrix material. Membranes containing Bio-Rex ® 70 and Chelex ® 100 were made with ethylene vinyl acetate having a 40 weight percent vinyl acetate content (EVA 40) as a matrix material. Membranes were made by solvent casting or melt processing. All membranes containing PVP-xl were made by standard melt processing techniques and all membranes containing Bio-Rex ® 70 were solvent cast from methylene chloride and dried at ambient conditions. Both methods of preparation were used for membranes containing Chelex ® 100. The transport properties of these composite membranes were evaluated as in Example I.

Figure 6:
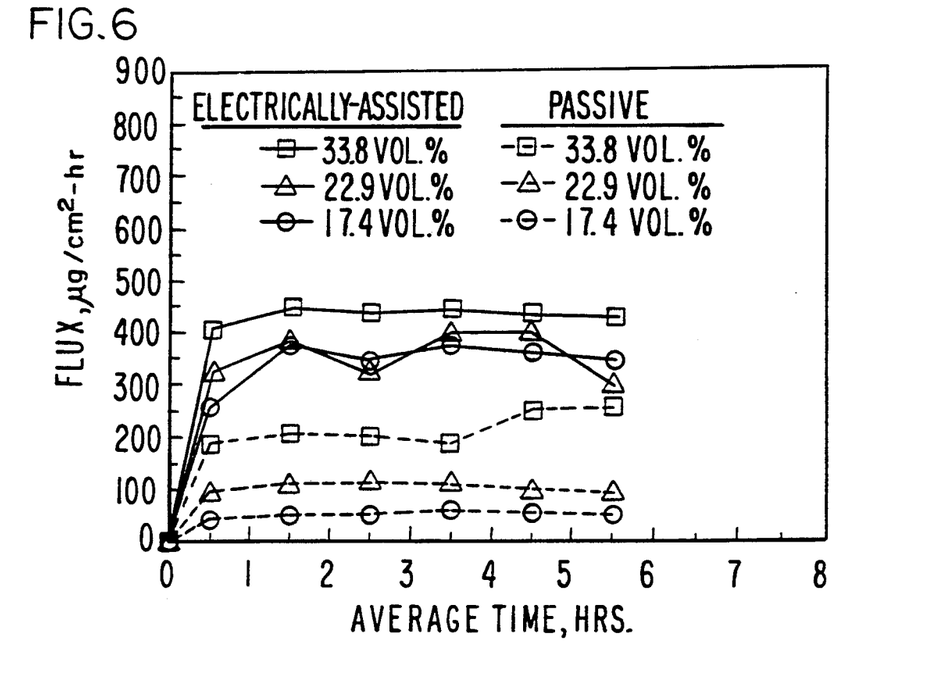
FIG. 6 is a graph comparing the electrically-assisted and passive flux of metoclopramide through membranes of this invention having various resin loadings.

Electrically-assisted and passive flux profiles of MCP through three volume loadings of Bio-Rex ® 70 in EVA 40 are shown in FIG. 6. Steady state was quickly achieved and a clear separation of electrically-assisted and passive transport was observed. Both electrically-assisted and passive steady state transport rates increased with increased resin loading.

The following table presents the $J_{EK}/J_P$ ratios for several of the membranes tested. The data represents the average steady state flux values.

TABLE I

| Polymer | Resin | Resin Loading, vol % | $J_{EK}/J_P$ Ratio |
|---|---|---|---|
| EVA 40 | Bio-Rex ® 70 | 17.4 | 6 |
|  |  | 22.9 | 2.5 |
|  |  | 33.8 | 1 |
| EVA 28 | PVP-xl | 12 | 6.4 |
|  |  | 18 | 0.9 |
|  |  | 25 | 0.4 |
|  |  | 34 | 0.3 |
| EVA 40 | Chelex ® 100 | 18.5 | 45 ± 17 |
|  | (100–200 mesh) | 24.2 | 20 ± 3 |
|  |  | 46.4 | 18 ± 3 |

Except for the 34 volume percent PVP-xl in EVA 28, the general trend was as the loading increased, so did the passive transport rate, while the electrokinetic transport remained relatively unchanged. Therefore, the $J_{EK}/J_P$ ratio decreased with increasing resin loading. The observed trend over the range of resins and volume loadings tested, was that for equivalent resin loadings, Chelex ® 100 exhibited larger $J_{EK}/J_P$ ratios than Bio-Rex ® 70, which in turn was better than PVP-xl. Both Chelex ® 100 and Bio-Rex ® 70 are cation exchange resins whereas PVP-xl will pick up a slight positive charge and act as an anion exchange resin. Since MCP is a positively charged drug, it was expected that MCP would have a larger transference number through anion exchange resins and therefore, a larger $J_{EK}/J_P$ ratio in Chelex ® 100 and Bio-Rex ® 70 membranes. Interestingly, Bio-Rex ® 70 has a higher fixed charge density than Chelex ® 100, yet it exhibited lower $J_{EK}/J_P$ ratios. We believe that this is due to the fact that Chelex ® 100 is an iminodiacetic acid meaning that two negative charges exist in very close proximity to one another, thus creating a local region of high electric field whereas the charge distribution within Bio-Rex ® 70 is uniform. This must play an important role in the selectivity of Chelex ® 100 for MCP transport and thereby increase the transference number of MCP.

When membranes are solvent cast from methylene chloride, the resin is added to the EVA/solvent mixture in wet (completely hydrated) form. When membranes are melt processed, the resin is first dried, then blended, melt pressed and finally the resultant film is rehydrated. We have found that the membranes obtained using these two processes have similar transport characteristics. We have also studied the effect of resin particle size and found that both Chelex ® 100 (100-200 mesh) and Chelex ® 100 (<400 mesh) exhibit an electrically-assisted steady state flux of about 300 μg/cm²—hr. However, the larger particle size gives appreciably higher passive flux than the small particles. It is believed that this is because the large particles were of the same size as the thickness of the membrane and therefore a single particle could span the film providing a relatively large continuous pathway. For the smaller particles, several particles have to contact each other to provide a continuous pathway. These contacts were more than likely at small points and therefore appeared as restrictions and provided a more tortuous diffusion pathway thereby reducing the passive flux.

EXAMPLE IV

The relationship between steady state electrically-assisted transport, the $J_{EK}/J_P$ ratio and the current density, was evaluated and found to be linear. This was established by testing an 18 volume Chelex ® 100 (<400 mesh)/EVA 40 composite membrane. The results obtained showed a linear relationship. Table II shows the range of measured resistivities and of the average measured flux values for MCP.

TABLE II

| Current Density μA/cm² | Resistivity kΩ-cm² | Flux μg/cm²-hr |
| --- | --- | --- |
| 50 | 1.4 | 73 |
| 100 | 2.9 | 142 |
| 200 | 3.6 | 276 |
| 300 | 29.0 | 441 |
| 417 | 2.4 | 644 |
| 625 | 10.6 | 948 |

Although this data has some fluctuations, four of the six resistivities measured were favorably less than the maximum desired or acceptable limit set at 10 kΩ—cm² for use as a rate controlling membrane.

The magnitude of the passive transport is dependent on the volume fraction of resin within the membrane. However, the electrically-assisted transport is independent of this quantity. Therefore, the $J_{EK}/J_P$ ratio can be predicted from the volume fraction of resin and other measurable quantities. This is illustrated in the following example.

EXAMPLE V

Figure 7:
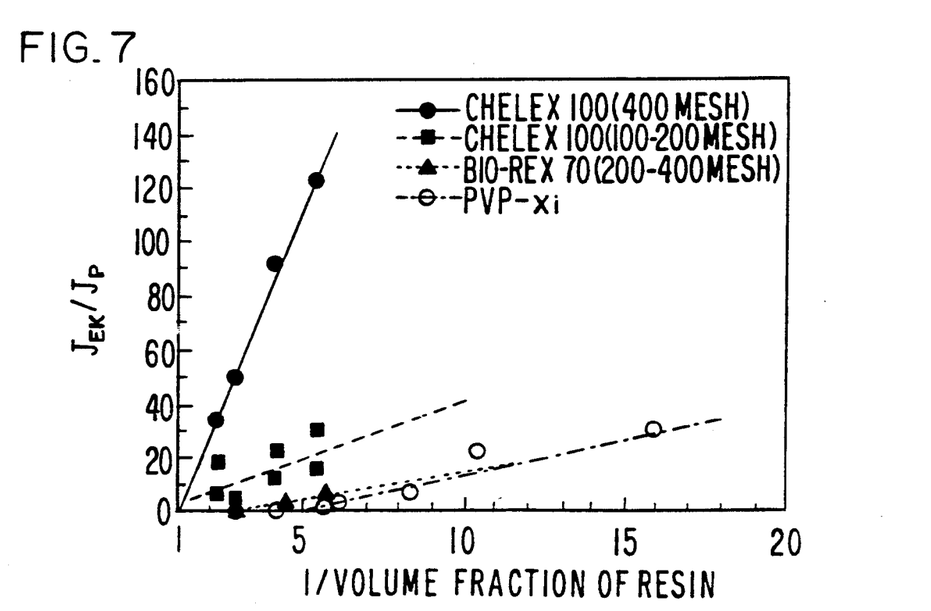
FIG. 7 is a graph illustrating the effect of resin loading on the $J_{EK}/J_P$ ratio of metoclopramide through various membrane compositions of this invention.

Four hydrophilic resins were studied using an EVA 40 matrix: Chelex ® 100 (<400 mesh), Chelex ® 100 (100-200 mesh), Bio-Rex ® 70 and PVP-xl. Equation (11) was used to compare the $J_{EK}/J_P$ ratios for various compositions of these composite membranes. The $J_{EK}/J_P$ ratio for each composition was calculated versus the volume fraction (1/volume value) and the results are presented in FIG. 7. All membranes showed a linear relationship when plotted in this form. The ordinate of this plot originates at 1 because it is physically impossible to have volume fractions greater than 1, i.e., 1/Θ can never be less than 1. Only positive valued intercepts are meaningful in FIG. 7. A positive y-intercept indicates that a membrane made of pure ion exchange resin has some capacity to retard passive transport. The value of a positive x-intercept indicates at what resin loading the passive component of the flux greatly outweighs the electrokinetic transport. A resin that retards passive transport at high loadings is desirable. The slopes of the resulting linear regression best fit lines are presented in Table III. It is possible to compare the slopes directly because all experimental parameters (temperature, donor concentration, current density and membrane thickness) were identical in the determination of the $J_{EK}/J_P$ ratios plotted in FIG. 7. It is apparent that the small particle size Chelex ® 100 is the most selective for MCP.

TABLE III

| Resin | Slope |
| --- | --- |
| Chelex ® 100 (<400 mesh) | 28.5 |
| Chelex ® 100 (100-200 mesh) | 4.03 |
| Bio-Rex ® 70 | 1.96 |
| PVP-xl | 2.87 |

The only anomaly in Table III is that it appears that the ability of membranes containing PVP-xl to control the passive flux of MCP is better than those containing Bio-Rex ® 70. It is true that Bio-Rex ® 70 is better at higher volume fractions, but the slope, for PVP-xl is higher and therefore, at low volume fractions, the $J_{EK}/J_P$ ratio is higher for PVP-xl membranes than for those containing Bio-Rex ® 70.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An iontophoretic agent delivery electrode assembly adapted for placement on a body surface for iontophoretic delivery of an analgesic drug therethrough, the electrode assembly including an electrode, a means for connecting said electrode to a source of electrical power, and a drug reservoir electrically connected to the electrode, the drug reservoir containing an analgesic drug in a form susceptible to iontophoretic delivery through the body surface, the drug being selected from the group consisting of fentanyl, sufentanil, analogues of fentanyl, analogues of sufentanil and pharmaceutically acceptable salts thereof.

2. The electrode assembly of claim 1, wherein the analgesic drug comprises a water soluble fentanyl salt.

3. The electrode assembly of claim 1, wherein the analgesic drug comprises a water soluble sufentanil salt.

4. The electrode assembly of claim 1, wherein the source of electrical power provides a current density of about 50 to 625 μA/cm².

5. The electrode assembly of claim 1, wherein the source of electrical power provides a current density of about 100 μA/cm².

6. The electrode assembly of claim 1, wherein the drug comprises fentanyl or a pharmaceutically acceptable analogue of fentanyl of a salt thereof.

7. The electrode assembly of claim 1, wherein the drug comprises sufentanil or a pharmaceutically acceptable analogue of sufentanil or a salt thereof.

8. An electrically powered iontophoretic delivery device including a donor electrode assembly adapted to be placed in drug transmitting relation with a body surface, a counter electrode assembly adapted to be placed in agent transmitting relation with a body surface and a source of electrical power adapted to be electrically connected to the donor electrode assembly and the counter electrode assembly, wherein the donor electrode assembly contains an ionized or ionizable source of an analgesic drug selected from the group consisting of fentanyl, sufentanil, analogues of fentanyl, analogues of sufentanil and pharmaceutically acceptable salts thereof.

9. The device of claim 8, wherein the drug comprises fentanyl or a pharmaceutically acceptable analogue of fentanyl or a salt thereof.

10. The device of claim 8, wherein the drug comprises sufentanil or a pharmaceutically acceptable analogue of sufentanil or a salt thereof.

11. The device of claim 8, wherein the source of electrical power provides a current density of about 50 to 625 $\mu A/cm^2$.

12. The device of claim 8, wherein the source of electrical power provides a current density of about 100 $\mu A/cm^2$.

13. A method of inducing analgesia, comprising:
placing an electrotransport agent delivery electrode assembly on a body surface, the electrode assembly including a drug reservoir and a means for electrically connecting said drug reservoir to a source of electrical power, the drug reservoir containing an analgesic drug in a form susceptible to electrotransport delivery through the body surface, the drug being selected from the group consisting of fentanyl, sufentanil, analogues of fentanyl, analogues of sufentanil and pharmaceutically acceptable salts thereof;
electrically connecting the drug reservoir to the source of electrical power;
placing the drug reservoir in drug-transmitting relation with the body surface; and
delivering the analgesic drug through the body surface by means of electrotransport, the drug being delivered at a rate sufficient to induce analgesia.

14. The method of claim 13, wherein the analgesic drug comprises a water soluble fentanyl salt.

15. The method of claim 13, wherein the analgesic drug comprises a water soluble sufentanil salt.

16. The method of claim 13, wherein the source of electrical power provides a current density of about 50 to 625 $\mu A/cm^2$.

17. The method of claim 13, wherein the source of electrical power provides a current density of about 100 $\mu A/cm^2$.

18. The method of claim 13, wherein the drug comprises fentanyl or a pharmaceutically acceptable analogue of fentanyl or a salt thereof.

19. The method of claim 13, wherein the drug comprises sufentanil or a pharmaceutically acceptable analogue of sufentanil or a salt thereof.

20. A method of inducing analgesia in a human patient, comprising:
placing in drug transmitting relation with a body surface of the patient an electrically powered iontophoretic delivery device, the delivery device including a donor electrode assembly and a counter electrode assembly, the donor electrode assembly containing an ionized or ionizable source of an analgesic drug selected from the group consisting of fentanyl, sufentanil, analogues of fentanyl, analogues of sufentanil and pharmaceutically acceptable salts thereof;
placing the counter electrode assembly in ion transmitting relation with the body surface at a location spaced apart from the donor electrode assembly;
electrically connecting a source of electrical power to the donor electrode assembly and the counter electrode assembly; and
iontophoretically delivering the analgesic drug through the body surface at a rate sufficient to induce analgesia in the patient.

21. The method of claim 20, wherein the drug comprises fentanyl or a pharmaceutically acceptable analogue of fentanyl or a salt thereof.

22. The method of claim 20, wherein the drug comprises sufentanil or a pharmaceutically acceptable analogue of sufentanil or a salt thereof.

23. The method of claim 20, wherein the source of electrical power provides a current density of about 550 to 625 $\mu A/cm^2$.

24. The method of claim 20, wherein the source of electrical power provides a current density of about 100 $\mu A/cm^2$.

* * * * *

UNITED STATES PATENT AND TRADEMARK OFFICE
CERTIFICATE OF CORRECTION

PATENT NO. : 5,232,438
DATED : August 3, 1993
INVENTOR(S) : Theeuwes et al.

It is certified that error appears in the above-indentified patent and that said Letters Patent is hereby corrected as shown below:

On the title page, item [54] and column 1, lines 2 and 3, change "MEMBRANE FOR ELECTROTRANSPORT TRANSDERMAL DRUG DELIVERY" to read --TRANSDERMAL ELECTROTRANSPORT DELIVERY OF ANALGESIC DRUGS--.

Column 18, line 38, "550" should read --50--.

Signed and Sealed this

Nineteenth Day of April, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,232,438  
DATED : August 3, 1993  
INVENTOR(S) : Theeuwes et al.

Page 1 of 1

It is certified that error appears in the above-identified patent and that said Letters Patent is hereby corrected as shown below:

Title page,
Item [*] Notice, "May 22, 2007" should be replaced with -- October 3, 2008 --.

Signed and Sealed this

Twelfth Day of February, 2002

Attest:

JAMES E. ROGAN
*Attesting Officer*     *Director of the United States Patent and Trademark Office*

REEXAMINATION CERTIFICATE (4004th)

United States Patent [19]
Theeuwes et al.

[11] B1 5,232,438
[45] Certificate Issued Feb. 29, 2000

[54] TRANSDERMAL ELECTROTRANSPORT DELIVERY OF ANALGESIC DRUGS

[75] Inventors: Felix Theeuwes; J. Richard Gyory, both of Los Altos; Ronald P. Haak, Cupertino, all of Calif.

[73] Assignee: Alza Corporation, Palo Alto, Calif.

Reexamination Request:
No. 90/003,535, Aug. 19, 1994

Reexamination Certificate for:
Patent No.: 5,232,438
Issued: Aug. 3, 1993
Appl. No.: 07/898,618
Filed: Jun. 15, 1992

Certificate of Correction issued Apr. 19, 1994.

Related U.S. Application Data

[63] Continuation of application No. 07/648,269, Jan. 30, 1991, Pat. No. 5,169,382, which is a continuation of application No. 07/252,402, Oct. 3, 1988, Pat. No. 5,080,646.

[51] Int. Cl.[7] .................................................. A61N 1/30
[52] U.S. Cl. ............................ 604/20; 604/501; 607/149
[58] Field of Search ................................. 604/20, 49, 21, 604/501; 607/149–152

[56] References Cited

U.S. PATENT DOCUMENTS

| | | | |
|---|---|---|---|
| 4,474,570 | 10/1984 | Ariura et al. | 604/20 |
| 4,588,580 | 5/1986 | Gale et al. | 424/21 |
| 4,752,285 | 6/1988 | Petelenz et al. | 604/21 |
| 4,764,164 | 8/1988 | Sasaki | 604/20 |

FOREIGN PATENT DOCUMENTS

62-135435  6/1987  Japan .

OTHER PUBLICATIONS

"American Drug Index" 25th ed, Billups, 1981 pp. 258–259.

Banga et al, Iontophoretic delivery of Drugs: Fundamentals, Developments and Biomedical Applications, Journal of Controlled Release, 7 (1988), pp. 1–24.

Gangarosa et al, Conductivity of Drugs Used for Iontophoresis, Journal of Pharmaceutical Sciences, vol. 67, No. 10, (Oct. 1978), pp. 1439–1443.

Gatipon, Morphine and Brain Stem Neurons: Microiontophoretic Study of Responses to Noxious Stimulation in the Cat, The Pharmacologist, Dept. Pharmacol. and Toxicol., Univ. Miss. Med. Ctr., Jackson, Ms. 39216, (1976), p. 177.

Hewson et al, The Effects of Anilidopiperidine Analgesics on Single Respiratory and Non–Respiratory Neurones in the Brain Stem of the Rat, Life Science, vol. 31, (1982), pp. 2335–2338.

Sebel et al, Transdermal Absorption of Fentanyl and Sufentanil in Man, European Journal of Clinical Pharmacology, vol. 32, (1987), pp. 529–531.

Stanley, New Routes of Administration and New Delivery Systems of Anesthetics, The Joural of Anesthesiology, vol. 68, No. 5, (May 1988), pp. 665–668.

Tyle, Iontophoretic Devices for Drug Delivery, Pharmaceutical Research, vol. 3, No. 6, (1986), pp. 318–326.

*Primary Examiner*—Mark Bockelman

[57] ABSTRACT

A membrane capable of inhibiting agent release from a delivery system when no electrical current is flowing and yet provide minimal impedance to electrically-assisted agent delivery, useful both for incorporating into electrotransport agent delivery systems and for use in measuring agent release rates in in vitro testing.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 8, 13, 20 are determined to be patentable as amended.

Claims 2-7, 9-12, 14-19, 21-24, dependent on an amended claim, are determined to be patentable.

1. An iontophoretic agent delivery electrode assembly adapted for placement on [a body surface] *intact skin of a living animal* for iontophoretic delivery of an analgesic drug therethrough, the electrode assembly including an electrode, a means for connecting said electrode to a source of electrical power, and a drug reservoir electrically connected to the electrode, the drug reservoir containing an analgesic drug in a form susceptible to iontophoretic delivery through the [body surface] *intact skin and into the animal*, the drug being selected from the group consisting of fentanyl, sufentanil, analogues of fentanyl, analogues of sufentanil and pharmaceutically acceptable salts thereof.

8. An electrically powered iontophoretic delivery device *for delivering a drug into a living animal body through intact skin, the device* including a donor electrode assembly adapted to be placed in drug transmitting relation with [a body surface] *the skin of the animal*, a counter electrode assembly adapted to be placed in agent transmitting relation with [a body surface] *the skin of the animal* and a source of electrical power adapted to be electrically connected to the donor electrode assembly and the counter electrode assembly, wherein the donor electrode assembly contains an ionized or ionizable source of an analgesic drug selected from the group consisting of fentanyl, sufentanil, analogues of fentanyl, analogues of sufentanil and pharmaceutically acceptable salts thereof.

13. A method of inducing analgesia, comprising:

placing an electrotransport delivery electrode assembly on [a body surface] *intact skin of a living animal body*, the electrode assembly including a drug reservoir and a means for electrically connecting said drug reservoir to a source of electrical power, the drug reservoir containing an analgesic drug in a form susceptible to electrotransport delivery through the [body surface] *skin*, the drug being selected from the group consisting of fentanyl, sufentanil, analogues of fentanyl, analogues of sufentanil and pharmaceutically acceptable salts thereof;

electrically connecting the drug reservoir to the source of electrical power;

placing the drug reservoir in drug-transmitting relation with the [body surface] *skin*; and delivering the analgesic drug through the *skin and into the body* [surface] by means of electrotransport, the drug being delivered at a rate sufficient to induce analgesia.

20. A method of inducing analgesia in a human patient, comprising:

placing in drug transmitting relation with [a body surface] *intact skin* of the patient an electrically powered iontophoretic delivery device, the delivery device including a donor electrode assembly and a counter electrode assembly, the donor electrode assembly containing an ionized or ionizable source of an analgesic drug selected from the group consisting of fentanyl, sufentanil, analogues of fentanyl, analogues of sufentanil and pharmaceutically acceptable salts thereof;

placing the counter electrode assembly in ion transmitting relation with the [body surface] *skin* at a location spaced apart from the donor electrode assembly;

electrically connecting a source of electrical power to the donor electrode assembly and the counter electrode assembly; and iontophoretically delivering the analgesic drug through the [body surface] *skin and into the patient* at a rate sufficient to induce analgesia in the patient.

* * * * *